United States Patent [19]

Patchen et al.

[11] Patent Number: 6,117,850
[45] Date of Patent: Sep. 12, 2000

[54] MOBILIZATION OF PERIPHERAL BLOOD PRECURSOR CELLS BY β(1,3)-GLUCAN

[75] Inventors: Myra L. Patchen, Framingham; Paul Bleicher, Newton, both of Mass.

[73] Assignee: The Collaborative Group, Ltd., Stony Brook, N.Y.

[21] Appl. No.: 08/647,352

[22] Filed: May 9, 1996

Related U.S. Application Data

[60] Provisional application No. 60/002,740, Aug. 28, 1995.

[51] Int. Cl.⁷ .................................................. A61K 31/70
[52] U.S. Cl. .............................................. 514/54; 514/21
[58] Field of Search ........................................ 514/54, 21

[56] References Cited

U.S. PATENT DOCUMENTS

| | | | |
|---|---|---|---|
| 4,739,046 | 4/1988 | DiLuzio | 536/117 |
| 4,761,402 | 8/1988 | Williams et al. | 514/54 |
| 5,532,223 | 7/1996 | Jamas et al. | 574/54 |
| 5,554,512 | 9/1996 | Lyman et al. | 435/69.5 |
| 5,637,323 | 6/1997 | Wiltrout et al. | 424/534 |

FOREIGN PATENT DOCUMENTS

| | | |
|---|---|---|
| WO 91/03248 | 3/1991 | WIPO . |
| WO 92/13896 | 8/1992 | WIPO . |
| WO 94/04163 | 3/1994 | WIPO . |

OTHER PUBLICATIONS

Czop, J.K., et al., "Perturbation of β–Glucan Receptors on Human Neutrophils Initiates Phagocytosis and Leukotriene $B_4$ Production", *J. of Immunology*, 141 (9):3170–3176 (1988).

Abel, G., and Czop, J.K, "Stimulation of Human Monocyte β–Glucan Receptors by Glucan Particles Induces Production of TNF–α and IL–1β", *Intl. J. Immunopharmacol.*, 14(8):1363–1373 (1992).

Doita, M., et al., "Effect of Soluble Aminated β–1, 3–d–Polyglucose on Human Monocytes: Stimulation of Cytokine and Prostaglandin $E_2$ Production But Not Antigen–Presenting Function", *J. of Leukocyte Biology*, 49:342–351 (1991).

Cain, J.A., et al., "Role of Complete Receptor Type Three and Serum Opsonins in the Neutrophil Response to Yeast", *Complement*, 4:75–86 (1987).

Gallin, E.K., et al., "Comparative Effects of Particulate and Soluble Glucan on Macrophages of C3H/HeN and C3H/HeJ Mice", *Int. J. Immunopharmacol.*, 14:173–183 (1992).

Brunke–Reese, D. and Mackin, W.M., "Enhanced Nitric Oxide (NO) Production by Peritoneal Macrophages Isolated from Rats Treated with PGG–Glucan (Betafectin™)", *Faseb J.*, 8:A216 Abstract No. 1244 (1994).

Poutsiaka, D.D., et al., "Cross–Linking of the β–Glucan Receptor on Human Monocytes Results in Interleukin–1 Receptor Antagonist but not Interleukin–1 Production", *Blood*, 82(12):3695–3700 (1993).

Wakshull, E., et al., "Synergistic Stimulation of Myeloid Progenitor Cell Proliferation by a Novel β–Glucan and GM–CSF", *J. Cell Biochem. Suppl.*, 18:A222 (1994).

Mackin, W., et al., "Enhanced Microbicidal Activities of Human Peripheral Blood Monocytes and Neutrophils (PMN) After Pre–Treatment with PGG–Glucan, (Betafectin)", *Faseb J.*, 8:A488, Abstract No. 2827 (1994).

Diamond, M.S., et al., "The I Doman is a Major Recognition Site on the Leukocyte Integrin Mac–1 (CD11b/CD18) for Four Distinct Adhesion Ligands", *J. Cell. Biol.*, 120(4):1031–1043 (1993).

Wakshull, E., et al., "Characterization of PGG–Glucan Bindings to a β–Glucan Receptor on Human Leukocytes", *Faseb J.*, 10:A1338, Abstract No. 1954 (1996).

Czop, J.K., et al., "Isolation and Characterization of β–Glucan Receptors on Human Mononuclear Phagocytes", *J. Exp. Med.*, 173:1511–1520 (1991).

Szabó, T., et al., "Biochemical Properties of the Ligand–Binding 20–kDa Subunit of the β–Glucan Receptors on Human Mononuclear Phagocytes", *J. of Biological Chemistry*, 270 (5):2145–2151 (1995).

Goldman, R., "Induction of a β–1, 3–D–Glucan Receptor in P388D1 Cells Treated with Retinoic Acid or 1,25–Dihydroxyvitamin $D_3$", *Immunology*, 63(2):319–324 (1988).

Goldman, R., "Characteristics of the β–Glucan Receptor of Murine Macrophages", *Experimental Cell Research*, 174(2):481–490 (1988).

Thornton, B.P., et al., "Analysis of the Sugar Specificity and Molecular Location of the β–Glucan–Binding Lectin Site of Complement Receptor Type 3 (CD11b/cd18)[1]", *J. Immunol.*, 156(3):1235–1246 (1996).

Konopski, Z, et al., "A Novel Immunomodulator Soluble Aminated β–1,3–D–Glucan: Binding Characteristics to Mouse Peritoneal Macrophages", *Biochem., Biophys. Acta*, 1221(1):61–65 (1994).

Müller, A., et al., "Receptor Binding and Internalization of a Water–Soluble (1→3)–β–D–Glucan Biologic Response Modifier in Two Monocyte/Macrophage Cell Lines[1]", *J. Immunol.*, 156:3418–3425 (1996).

Engstad R.E., et al., "Specificity of a β–Glucan Receptor on Macrophages from Atlantic Salmon (Salmo Salar L.)", *Dev. Comp. Immunol.*, 18(5):397–408 (1994).

Muller, C.D., et al., "Functional β–Glucan Receptor Expression by a Microglial Cell Line", *Res. Immunol.*, 145:267–275 (1994).

(List continued on next page.)

*Primary Examiner*—Elli Peselev
*Attorney, Agent, or Firm*—Hamilton, Brook, Smith & Reynolds, P.C.

[57] ABSTRACT

Methods for inducing mobilization of peripheral blood precursor cells, for elevating levels of peripheral blood precursor cells and facilitating hematopoietic reconstitution in a mammal are disclosed, comprising administering to the mammal an effective amount of an underivatized, aqueous soluble β(1,3)-glucan in a triple helix conformation, which does not stimulate or prime the production of proinflammatory cytokines in vitro.

22 Claims, 6 Drawing Sheets

OTHER PUBLICATIONS

Czop, J.K., et al., "Production and Isolation of Rabbit Anti–Idiotypic Antibodies Directed Against the Human Monocyte Receptor for Yeast β–Glucans", *J. of Immunology,* 45:955–1001 (1990).

Demirer, T., "Optimization of Peripheral Blood Stem Cell Mobilization", *Stem Cells,* 14:106–116 (1996).

Stadtmauer, E.A., et al., "Peripheral Blood Progenitor Cell Generation and Harvesting", *Seminars in Oncology,* 22(3):291–300 (1995).

Browder, W., et al., "Beneficial Effect of Enhanced Macrophage Function in the Trauma Patient", *Ann. Surg.,* 211(5):605–613 (1990).

Chihara, G., et al., "Lentinan as a Host Defence Potentiator (HDP)", *Int. J. Immunotherapy,* (4):145–154 (1989).

Pretus, H.A., et al., "Isolation, Physicochemical Characterization and Preclinical Efficacy Evaluation of Soluble Scleroglucan", *J. of Pharmacology and Experimental Therapeutics,* 500–510 (1991).

Williams, D.L., et al., "Development, Physicochemical Characterization and Preclinical Efficacy Evaluation of a Water Soluble Glucan Sulfate Derived From *Saccharomyces Cerevisiae*", *Immunopharmacology,* 22:139–156 (1991).

Patchen, M.L. and MacVittie, T.J., "Temporal Response of Murine Pluripotent Stem Cells and Myeloid and Erythroid Progenitor Cells to Low–Dose Glucan Treatment", *Acta heamat.,* 70:281–288 (1983).

Patchen, M.L., et al., "Mobilization of Peripheral Blood Progenitor Cells by Betafectin PGG–Glucan", *Experimental Hematology,* 24 Abstract No. 43 (1996).

Patchen, M.L. and Lotzová, Modulation of Murine Hemopoiesis by Glucan, *Exp. Hemat.,* 8(4):409–422 (1980).

MOBILIZATION OF PERIPHERAL BLOOD PRECURSOR CELLS BY β(1,3)-GLUCAN

RELATED APPLICATION

This application is a Continuation-in-Part of copending U.S. Provisional application Ser. No. 60/002,740, filed Aug. 28, 1995, entitled "Mobilization of Peripheral Blood Precursor Cells By β(1,3)-Glucan", by Myra L. Patchen, et al., the entire teachings of which are incorporated herein by reference.

BACKGROUND OF THE INVENTION

Treatment of various cancers increasingly involves cytoreductive therapy, including high dose chemotherapy or radiation therapy. These therapies decrease a patient's white blood cell counts, suppress bone marrow hematopoietic activity, and increase their risk of infection and/or hemorrhage. As a result, patients who undergo cytoreductive therapy must also receive therapy to reconstitute bone marrow function (hematopoiesis). Current treatments to manage the problems that result from prolonged bone marrow suppression include the reinfusion of a patient's own previously harvested peripheral blood precursor cells (PBPC). In such procedures, patients undergo successive treatments with cell mobilization agents to cause mobilization of hematopoietic progenitor cells from the bone marrow to the peripheral circulation for harvesting. After harvesting, the patient is given high dose chemotherapy or radiotherapy and the bone marrow function is reconstituted by infusion of the cells harvested earlier.

Because of the small number of PBPC present in the blood, multiple cycles of mobilization of PBPC (movement of PBPC from the hematopoietic organs into the peripheral circulation) are required to collect a sufficient number of PBPC for transplantation. This method is costly, inconvenient for outpatients, and may be associated with adverse side effects. Furthermore, mobilization of PBPC may take many days. G-CSF and GM-CSF have been used to release stem cells from marrow to be harvested before chemotherapy; however, the treatment takes from 4 to 7, and up to 12 days, before appearance of the cells in the peripheral blood (see published PCT application WO 94/38916). Furthermore, some patients fail to mobilize PBPC following treatment with colony-stimulating factors.

Development of a method to enhance and accelerate PBPC mobilization and facilitate hematopoietic reconstitution would be highly desirable, especially for individuals who require transplantation of PBPC following cytoreductive therapy.

SUMMARY OF THE INVENTION

The present invention relates to methods for inducing mobilization of peripheral blood precursor cells (PBPC) from the hematopoietic organs of the body, such as bone marrow, liver, or spleen. The methods involve the administration of an underivatized, aqueous soluble β(1,3)-glucan to a mammal in an amount sufficient to mobilize PBPC. The invention also relates to methods for elevating circulating levels of peripheral blood precursor cells, by the administration of an underivatized, aqueous soluble β(1,3)-glucan to a mammal in an amount sufficient to mobilize PBPC and thereby elevate the levels of PBPC in the peripheral blood. The invention further relates to methods for enhancing or facilitating hematopoietic reconstitution or engraftment, by the administration of an underivatized, aqueous soluble β(1,3)-glucan. The invention is also related to methods for enhancing progenitor cell mobilization, by administering a growth factor, such as granulocyte colony stimulating factor (G-CSF), in combination with an underivatized, aqueous soluble β(1,3)-glucan. The invention further pertains to kits useful in the methods.

Underivatized, aqueous soluble β(1,3)-glucans useful for inducing mobilization of PBPC have been described in U.S. Ser. No. 08/373,251, filed Jan. 26, 1995, now U.S. Pat. No. 5,783,569; Ser. No. 07/934,015, filed Aug. 21, 1992, now U.S. Pat. No. 5,622,939; Ser. No. 08/060,418, filed May 11, 1993 now U.S. Pat. No. 5,488,040; and Ser. No. 08/452,971, filed May 30, 1995, now U.S. Pat. No. 5,532,223. the entire teachings of each of which are incorporated herein by reference. The underivatized, aqueous soluble β(1,3)-glucan can be administered parenterally (e.g., intravenously, intraperitoneally, subcutaneously, intramuscularly), topically, orally or intranasally to humans and animals. It can additionally be administered in a pharmaceutically acceptable vehicle. The methods of the current invention can be used to mobilize PBPC in patients who will undergo cellular transplantation to replace stem cells which have been depleted by cytoreductive therapy; to mobilize PBPC to be used for genetic alteration and reinjection for gene therapy; to mobilize PBPC to be used for allogenic transplantation; to cause tolerization of a recipient of an organ transplantation, by infusing enriched PBPC from the donor into the recipient; or to increase the number of engrafted cells, to decrease the time to engraftment, or to enhance the quality of engraftment in hematopoietic reconstitution.

DETAILED DESCRIPTION OF THE INVENTION

The invention is directed toward the discovery that an underivatized, aqueous soluble β(1,3)-glucan can induce mobilization of peripheral blood precursor cells (PBPC). It has been discovered that underivatized, aqueous soluble β(1,3)-glucan (poly-β(1−6)-glucotriosyl-β(1−3)-glucopyranose; PGG-glucan), induces mobilization of PBPC in an in vivo model. As described below, groups of mice were intravenously injected with saline, or underivatized, aqueous soluble β(1,3)-glucan, and blood obtained at times ranging from 30 minutes to 8 days later via cardiac puncture. The underivatized, aqueous soluble β(1,3)-glucan quickly mobilized hematopoietic progenitor cells into the peripheral blood in a dose-dependent manner following the intravenous administration. These results were confirmed in human studies, which demonstrated that intravenous administration of underivatized, aqueous soluble β(1,3)-glucan mobilized progenitor cells. Additional studies showed the repopulation potential of progenitor cells that were mobilized by administration of an underivatized, aqueous soluble β(1,3)-glucan was greater than that of control (non-mobilized) cells. Further experiments revealed that the combination of granulocyte colony stimulating factor (G-CSF) and underivatized, aqueous soluble β(1,3)-glucan enhanced progenitor cell mobilization beyond that of each agent alone.

As a result of these findings, methods have been developed to induce mobilization of peripheral blood precursor cells, to elevate circulating levels of peripheral blood precursor cells, or to enhance or facilitate hematopoietic reconstitution or engraftment, in mammals, including humans. "Peripheral blood precursor cells", as used herein, include stem cells, which are pluripotent, and early progenitor cells, which are more differentiated but have a greater potential for proliferation than stem cells.

In one embodiment of the current invention, mobilization of peripheral blood precursor cells in a mammal is induced by administering to the mammal an effective amount of an underivatized, aqueous soluble β(1,3)-glucan in a triple helix conformation, which does not stimulate or prime the production of proinflammatory cytokines in vitro. Underivatized, aqueous soluble β(1,3)-glucans useful for inducing mobilization of PBPC are described in U.S. Ser. No. 08/373,251, filed Jan. 26, 1995, and Ser. No. 07/934,015, filed Aug. 21, 1992, the entire teachings of which are incorporated herein by reference. "Proinflammatory cytokines," as used herein, include interleukin-1 and/or tumor necrosis factor.

In a second embodiment of the current invention, the level of circulating PBPC is elevated, particularly by the release and mobilization of PBPC, by administering to the mammal, an effective amount of an underivatized, aqueous soluble β(1,3)-glucan in a triple helix conformation, which does not stimulate or prime the production of proinflammatory cytokines in vitro.

In a third embodiment of the invention, hematopoietic reconstitution or engraftment is facilitated or enhanced by administering to the mammal, an effective amount of an underivatized, aqueous soluble β(1,3)-glucan in a triple helix conformation, which does not stimulate or prime the production of proinflammatory cytokines in vitro. The β(1,3)-glucan is administered at the same time as, or in close proximity to (e.g., within approximately 1 to 7 days), the cellular preparation containing hematopoietic progenitor or stem cells.

In a fourth embodiment of the invention, progenitor cell mobilization is enhanced, by administering to the mammal, an effective amount of an underivatized, aqueous soluble β(1,3)-glucan in a triple helix conformation, which does not stimulate or prime the production of proinflammatory cytokines in vitro, in conjunction with a growth factor, such as G-CSF, GM-CSF, IL-3, GM-CSF/IL-3 fusion proteins, FLK-2/FLT-3 ligand, IL-6, IL-11, TPO, SCF, or other growth factor. In a preferred embodiment, the growth factor is G-CSF. The term, "in conjunction with", as used herein, refers to concurrent administration of the β(1,3)-glucan with the growth factor, as well as administration of the β(1,3)-glucan within several days (e.g., within approximately 1 to 7 days) of administration of the growth factor. Administration of the growth factor can be before or after administration of the β(1,3)-glucan.

The underivatized, aqueous soluble β(1,3)-glucan is administered to an animal or a human in an effective amount, sufficient to mobilize PBPC, to elevate the level of circulating PBPC or facilitate hematopoietic reconstitution. The effective amount is determined on an individual basis, and will be based at least in part on consideration of the patient's overall health or condition, the patient's weight, and the time available before cytoreductive therapy or other treatment. Administration of the effective dose of β(1,3)-glucan can be in the form of a single dose, or a series of doses separated by intervals of hours, days or weeks. The term "single dose," as used herein, includes a solitary dose as well as a sustained release dose. In general, a single dose will preferably contain approximately 0.01 to approximately 200 mg of glucan per kilogram of body weight, and preferably from about 0.1 to 5.0 mg/kg.

The mode of administration of the underivatized, aqueous soluble β(1,3)-glucan can be oral, intravenous, subcutaneous, intraperitoneal, intramuscular, topical, intranasal, or a sustained release dose in dosage formulations containing conventional physiologically-acceptable carriers and vehicles.

The form in which the dosage formulation will be administered (e.g., powder, tablet, capsule, solution, emulsion) will depend at least in part on the route by which it is administered. The formulations can optionally include other components in addition to the underivatized, aqueous soluble β(1,3)-glucan. Other components are determined primarily by the manner in which the composition is to be administered. For example, a composition to be administered orally in tablet form can include, in addition to the glucan, a filler (e.g., lactose), a binder (e.g., carboxymethyl cellulose, gum arabic, gelatin), an adjuvant, a flavoring agent, a coloring agent and a coating material (e.g., wax or plasticizer). For administration in liquid form, an emulsifying agent, a flavoring agent and/or a coloring agent can be included in addition to the glucan. For parenteral administration, the glucan can be mixed, dissolved or emulsified in water, sterile saline, PBS, dextrose or other biologically acceptable carrier.

The underivatized, aqueous soluble β(1,3)-glucan can be administered alone, or in conjunction with other compounds which mobilize stem cells, such as growth factoris (G-CSF, GM-CSF, IL-3, GM-CSF/IL-3 fusion proteins, FLK-2/FLT-3 ligand, IL-6, IL-11, TPO or SCF); drugs, such as cyclophosphamide or 5-fluorouracil; and/or certain antibodies, such as anti-VLA4. Combinations of these other compounds can also be used.

The method of mobilizing PBPC can be used for mobilization of PBPC in patients who will undergo cytoreductive therapy, such as chemotherapy or radiation therapy. After mobilization, the PBPC are collected from the peripheral blood and either stored, or expanded in culture. Because the number of PBPC in the peripheral blood is increased by mobilization, the method reduces the number of harvesting procedures necessary. Mobilization of PBPC thus facilitates collection of a sufficient quantity of the patient's own PBPC for reinfusion. Furthermore, the short time frame between administration of the β(1,3)-glucan and mobilization of the PBPC also lessens delay to treatment, as the PBPC can be collected within a short time frame. The stored or expanded PBPC can be reinfused to restore the formation of bone marrow after high-dose chemotherapy or radiation therapy, using methods such as those described by Gillis (U.S. Pat. No. 5,199,942), and thus accelerate recovery of bone marrow function. In addition, harvesting of the cells protects the cells from the harmful effects of the treatment. The cells can be expanded after harvesting by administration of the β(1,3)-glucan, with or without a growth factor, to the cells in vitro. The aqueous soluble β(1,3)-glucan can also be administered, either with or without growth factors, at the time of autologous transplant to facilitate the reconstitution of hematopoietic progenitor cells.

The method of mobilizing PBPC can also be used for mobilization of PBPC in individuals who will serve as allogenic donors of PBPC. After mobilization, the PBPC are collected from the peripheral blood and either stored, or expanded in culture. Because the number of PBPC in the peripheral blood is increased by mobilization, the method reduces the number of harvesting procedures necessary. Mobilization of PBPC thus facilitates collection of a sufficient quantity of an individual's PBPC for transplantation.

Other diseases and disorders for which the β(1,3)-glucan is beneficial in addition to those already described are leukopenia of various origins including, congenital leukopenia, childhood or adult cyclic neutropenia, post-infective neutropenia, and myelodysplastic syndrome. In addition, the β(1,3)-glucan can be used for patients who are "difficult to mobilize" because, for example, they are not sensitive to growth factors.

The methods can additionally be used for gene therapy. Because pluripotent stem cells are self-renewing, and give rise to cell progenitors as well as mature blood cells, the stem cells are an appropriate target for gene therapy. After mobilization, PBPC can be collected. The PBPC can be modified to deliver gene products upon reintroduction to the individual. For example, cells of individuals affected with genetic diseases such as hemoglobinopathies (thalassemia, sickle cell anemia), coagulation factor deficiencies (hemophilia A), or other diseases (adenosine deaminase deficiency, recombinase deficiency) can be modified to insert a corrective gene. Alternatively, the mutant gene in the cells can be targeted for correction. After modification, the cells are reinfused into the affected individual. Alternatively, PBPC can be modified to deliver other gene products to the individual to correct other genetic defects or to make hematopoietic cells resistant to further chemotherapy (for example, with the MDR gene).

The methods can further be used to cause tolerization of a recipient for organ transplantation. Enriched PBPC from a donor are infused into a recipient such that a state of tolerance to a transplanted organ from the donor is induced (see published PCT application WO 95/04062).

The invention also pertains to kits useful in the methods of the invention. Such a kit contains an appropriate quantity of β(1,3)-glucan, and other components useful for the methods. For example, a kit used to facilitate ex vivo expansion of hematopoietic stem cells contains an appropriate amount of the β(1,3)-glucan to facilitate mobilization, as well as an amount of the β(1,3)-glucan to enhance the expansion of the stem cells by growth factors. Such a kit can also contain an appropriate amount of a growth factor.

The invention is further illustrated by the following Examples, which are not intended to be limiting in any way.

EXAMPLE 1 Effect of β(1,3)-glucan Administration on Mobilization of Peripheral Blood Precursor Cells Groups of C3H/HeN male mice were intravenously injected with saline, 0.5 mg/kg, 2.0 mg/kg, or 4.0 mg/kg of underivatized, aqueous soluble β(1,3)-glucan and blood obtained 30 minutes later via cardiac puncture. Peripheral blood mononuclear cells were separated on an LSME sucrose gradient and cultured for GM-CFC in the presence of 0.1 ng/ml recombinant murine GM-CSF (rmGM-CSF).

This short time frame is in sharp contrast to previous data, which indicates that at least several days are necessary for mobilization after administration of particulate glucan (Patchen and Lotzova, *Exp. Hemat.* 8(4):409–422 (1980); Patchen and MacVittie, *Acta Haematologica* 70:281–288 (1983)).

Figure 1:
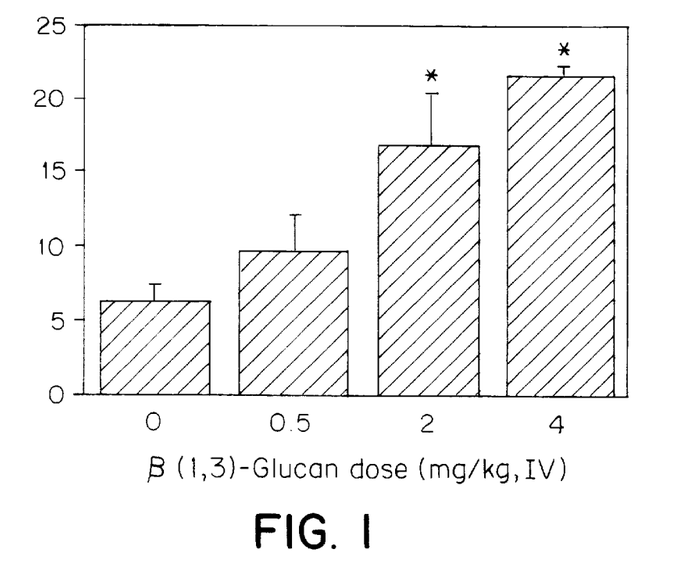
FIG. 1 is a graphic representation of the effect of underivatized, aqueous soluble β(1,3)-glucan on mobilization of GM-CFC thirty minutes after IV administration in mice. Data represent the mean +/− SEM of triplicate colony counts. * $P<0.05$, with respect to saline control values.

The underivatized, aqueous soluble β(1,3)-glucan mobilized hematopoietic progenitor cells into the peripheral blood in a dose-dependent manner following the intravenous glucan administration (FIG. 1). Compared to an average of 6.3+/−1.1 GM-CFC per $10^6$ peripheral blood mononuclear cells observed in the saline-treated mice, 9.8 +/−2.3, 16.9 +/−3.4, and 21.6 +/−0.5 GM-CFC per $10^6$ peripheral blood mononuclear cells were observed in mice treated with 0.5 mg/kg, 2.0 mg/kg and 4.0 mg/kg of underivatized, aqueous soluble β(1,3)-glucan, respectively. At the highest dose, this represented an approximate 3.5-fold increase in peripheral blood GM-CFC numbers.

Figure 2:
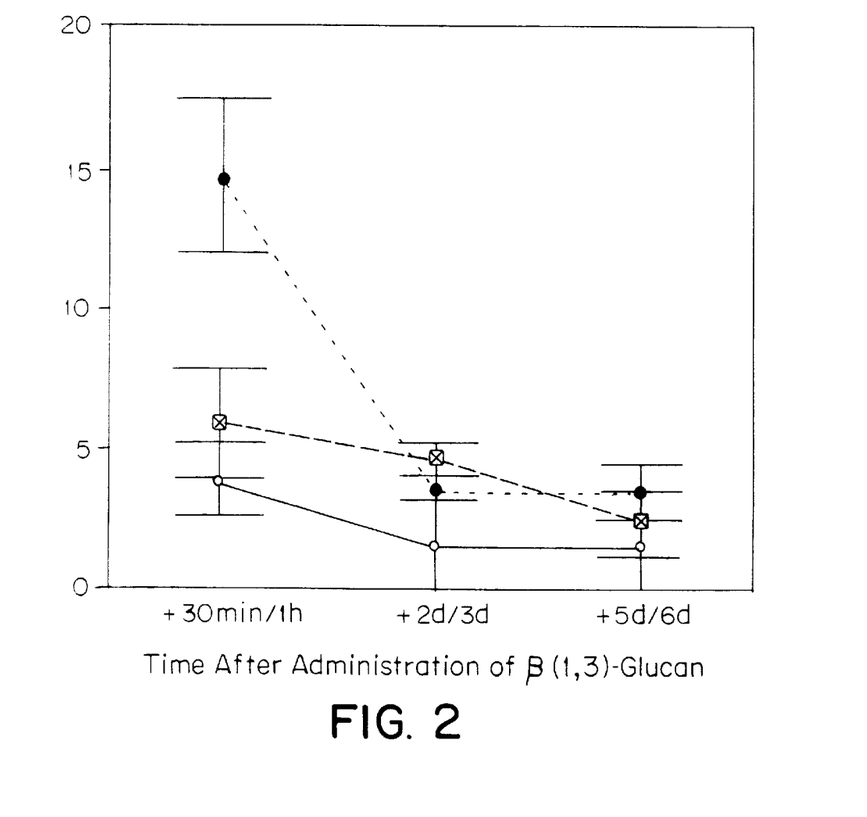
FIG. 2 is a graphic representation of the effect of underivatized, aqueous soluble β(1,3)-glucan on peripheral blood GM-CFC mobilization over time in mice. LDMNC= light density mononuclear cells. Small squares=saline control; large squares=0.5 mg/kg underivatized, aqueous soluble β(1,3)-glucan; circles=2.0 mg/kg underivatized, aqueous soluble β(1,3)-glucan. Each point represents data compiled from triplicate colony counts from 2–3 separate experiments.

The mobilization of progenitor cells following glucan treatment was transient. After underivatized, aqueous soluble β(1,3)-glucan was administered intravenously, mononuclear cells were collected at 30 min or 1 hour, 2 or 3 days, and 5 or 6 days. The cells were separated on an LSM® sucrose gradient and cultured for GM-CFC in the presence of 0.1 ng/ml recombinant murine GM-CSF. As shown in FIG. 2, GM-CFC numbers returned to near normal levels by approximately 48 hours after glucan administration.

Figure 3:
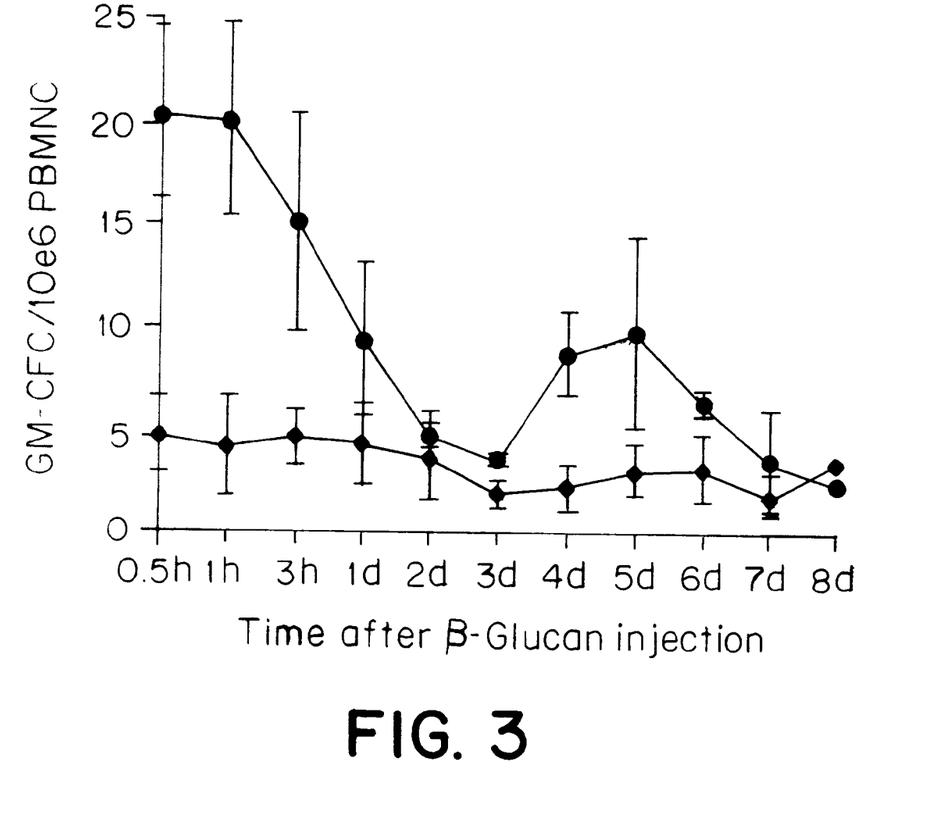
FIG. 3 is a graphic representation of the effect of β(1,3)-glucan on peripheral blood GM-CFC mobilization over time with mice. Diamonds=saline control; circles=2.0 mg/kg β(1,3)-glucan.

EXAMPLE 2 Mobilization of Peripheral Blood Progenitor Cells by Underivatized, Aqueous Soluble β(1,3)-glucan in Mice The time course and dose-dependence for underivatized, aqueous soluble β(1,3)-glucan-induced mobilization was evaluated. To determine the time course of mobilization, underivatized, aqueous soluble β(1,3)-glucan (2 mg/kg) was administered intravenously to C3H/HeN female mice, and blood collected via cardiac puncture from groups of 3–9 mice at times ranging from 30 minutes to 8 days after injection. Peripheral blood light density mononuclear cells (PBMNC) were separated on Ficoll and cultured for GM-CFC in the presence rmG-CSF. Data represent the mean +/− standard deviation of mean values obtained in 2–8 individual experiments. FIG. 3 illustrates that underivatized, aqueous soluble β(1,3)-glucan mobilized GM-CFC and that peak mobilization occurred thirty to sixty minutes after underivatized, aqueous soluble β(1,3)-glucan administration, with a second smaller wave of GM-CFC mobilization occurring on days 4–6 after underivatized, aqueous soluble β(1,3)-glucan treatment.

Figure 4A:
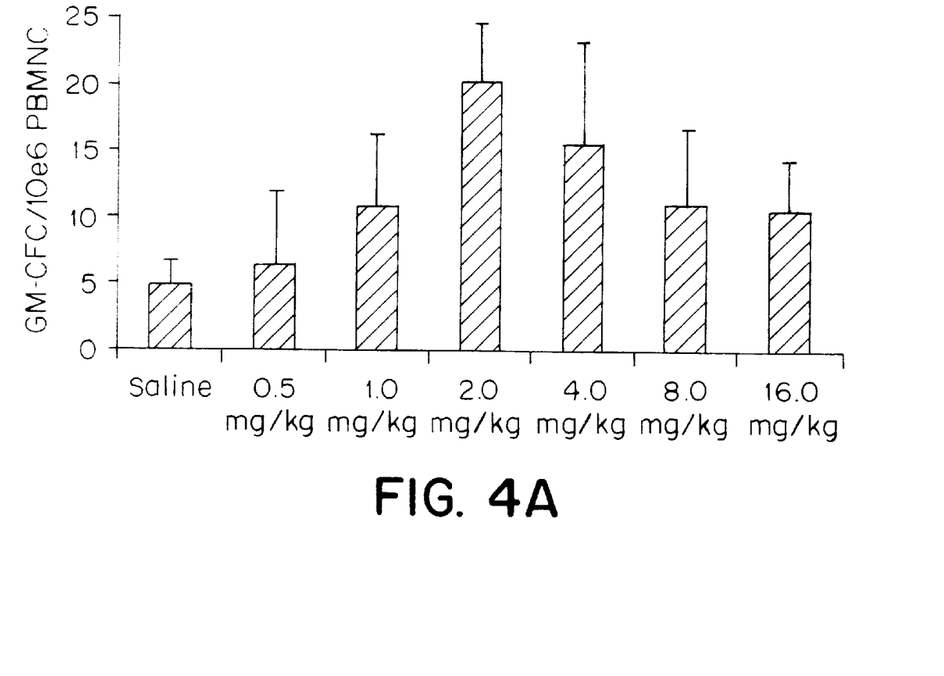
FIG. 4A is a graphic representation of the dose-response relationship for the mobilization of peripheral blood progenitor cells by β(1,3)-glucan at 30 minutes after administration.
Figure 4B:
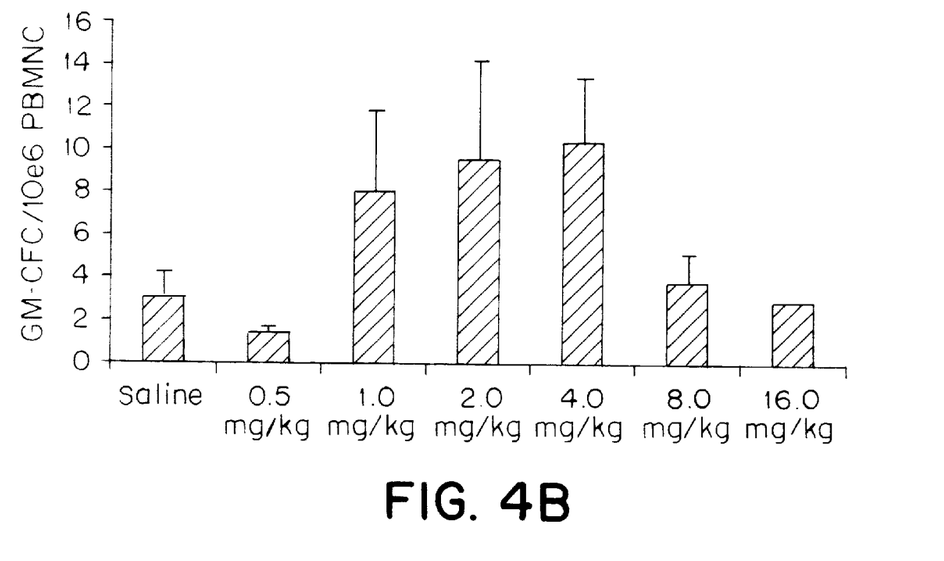
FIG. 4B is a graphic representation of the dose-response relationship for the mobilization of peripheral blood progenitor cells by β(1,3)-glucan at five days after administration.

To determine the dose-response relationship for the mobilization of peripheral blood progenitor cells, underivatized, aqueous soluble β(1,3)-glucan (0.5–16 mg/kg) was administered intravenously to C3H/HeN female mice and blood collected from groups of 3–9 mice at either 30 minutes (FIG. 4A) or five days (FIG. 4B) after injection. PBMNC were separated on Ficoll and cultured for GM-CFC as described above. Data represent the mean +/− standard deviation of mean values obtained in 3–8 individual experiments. The responses at each time were dose-dependent, with optimal mobilization observed at 2–4 mg/kg of underivatized, aqueous soluble β(1,3)-glucan.

Figure 5:
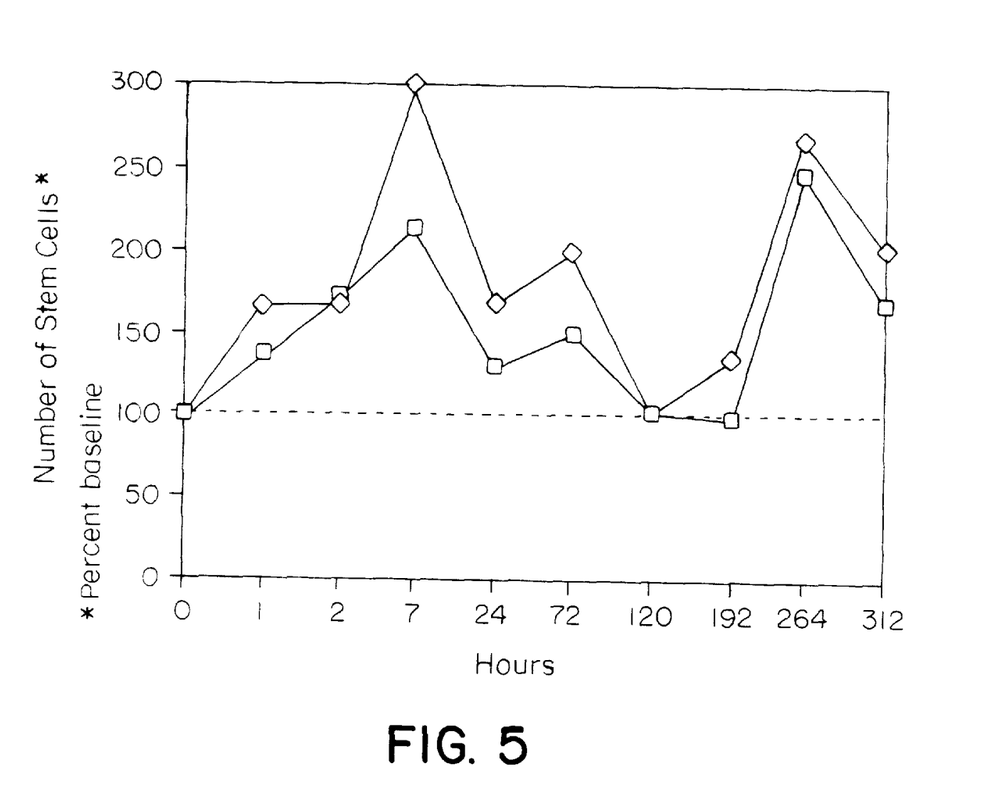
FIG. 5 is a graphic representation of the effect of β(1,3)-glucan on peripheral blood GM-CFC mobilization and CD34+ progenitor cells over time in a human subject receiving 0.75 mg/kg β(1,3)-glucan. Circles=CD34+ progenitor cells, squares=GM-CFC.

EXAMPLE 3 Time Course of the Mobilization of Peripheral Blood Progenitor Cells by Underivatized. Aqueous Soluble β(1,3)-glucan in Normal Human Volunteers A randomized, double-blind, placebo-controlled clinical trial was conducted in healthy males to evaluate the ability of underivatized, aqueous soluble β(1,3)-glucan to mobilize PBPC. Underivatized, aqueous soluble β(1,3)-glucan was administered as a single, intravenous infusion of 0.75, 1.5 or 2.5 mg/kg. Saline was administered as the placebo control. Venous blood was collected at various times following administration of saline or underivatized, aqueous soluble β(1,3)-glucan. The PBPC mobilization potential of underivatized, aqueous soluble β(1,3)-glucan was evaluated based on peripheral GM-CFC levels and peripheral blood CD34+ mononuclear cells (a surrogate progenitor cell marker). The time course of the mobilization for a subject receiving 0.75 mg/kg is shown in FIG. 5. In normal volunteers, mobilization of CD34+ and GM-CFC was observed within 7 hours of underivatized, aqueous soluble β(1,3)-glucan infusion which was followed by a second wave of mobilization on day 11.

Figure 6:
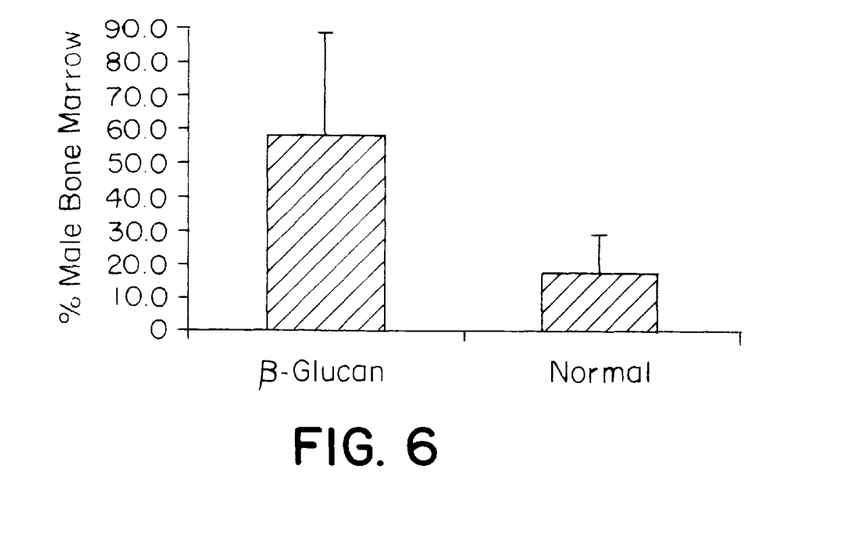
FIG. 6 is a graphic representation of the reconstitutional potential of progenitor cells mobilized by β(1,3)-glucan in lethally irradiated mice. Normal=saline control.

EXAMPLE 4 Repopulation Potential of Progenitor Cells Mobilized by Underivatized, Aqueous Soluble β(1,3)-glucan in Mice The quality of the progenitor cells mobilized by underivatized, aqueous soluble β(1,3)-glucan was evaluated based on the reconstitutional potential of these cells in lethally irradiated mice. Equal numbers of peripheral blood mononuclear cells isolated from C3H/HeN male mice 30 minutes after either saline or underivatized, aqueous soluble β(1,3)-glucan treatment were injected intravenously into lethally irradiated (8.5 Gy) C3H/HeN female mice. At three weeks after transplantation, the ability of the injected cells to reconstitute the bone marrow of the recipient animals was determined using Southern blot analysis with a Y-chromosome specific probe. Data are presented in FIG. 6 and represent the mean +/− standard deviation of values obtained from three recipient mice in each treatment group. Three weeks after transplantation, the bone marrow in animals transplanted with cells from saline (Normal)-treated mice contained only 5%–23% (mean 17%) male DNA, while 36%–93% (mean 58%) male DNA was detected in the bone marrow of animals transplanted with cells from underivatized, aqueous soluble β(1,3)-glucan-treated mice, indicating greater reconstitutional potential in the underivatized, aqueous soluble β(1,3)-glucan mobilized progenitor cells.

Figure 7:
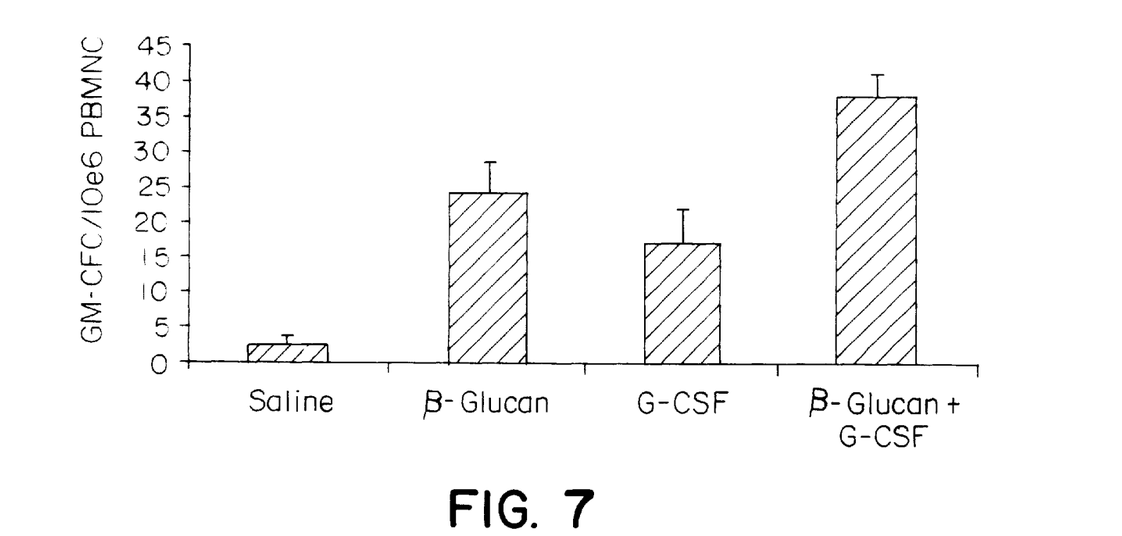
FIG. 7 is a graphic representation of mobilization of peripheral blood progenitor cells by G-CSF and β(1,3)-glucan in mice. Saline=saline alone; β(1,3)-glucan=2 mg/kg underivatized, aqueous soluble β(1,3)-glucan on day 0; G-CSF=125 ug/kg/day on days −3, −2, and −1; and β(1,3)-glucan+G-CSF, G-CSF=125 ug/kg/day on days −3, −2, and −1 and 2 mg/kg underivatized, aqueous soluble β(1,3)-glucan on day 0.

EXAMPLE 5 Mobilization of Peripheral Blood Progenitor Cells by the Combination of Recombinant Human Granulocyte Colony Stimulating Factor (G-CSF) and Underivatized. Aqueous Soluble β(1,3)-glucan in Mice Groups of three C3H/HeN female mice were injected for three consecutive days (days −3, −2, −1) with G-CSF (125 ug/kg/d, subcutaneously) alone; injected on day 0 with underivatized, aqueous soluble β(1,3)-glucan (2 mg/kg, intravenously) alone; injected on days −3, −2, and −1 with G-CSF (125 ug/kg/d, subcutaneously) and on day 0 with underivatized, aqueous soluble β(1,3)-glucan (2 mg/kg, intravenously); or injected with saline. On day 0, blood was collected 30 minutes after underivatized, aqueous soluble β(1,3)-glucan treatment and PBMNC were separated and cultured for GM-CFC as described in Example 2. Data represent the mean +/− standard deviation of triplicate cultures and are shown in FIG. 7. When underivatized, aqueous soluble β(1,3)-glucan was administered to mice injected for three consecutive days with G-CSF, the number of GM-CFC detected was additive between that detected in mice treated with only G-CSF and that detected in mice treated only with underivatized, aqueous soluble β(1,3)-glucan.

Figure 8:
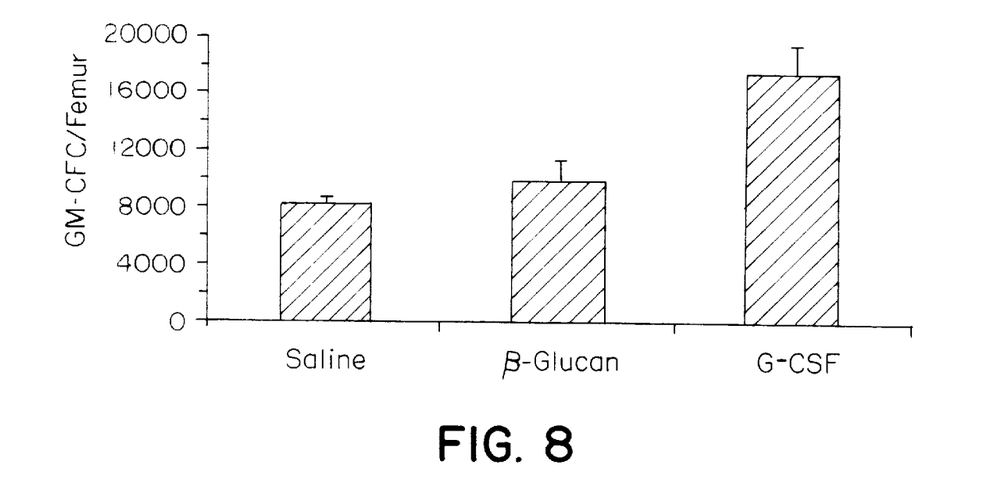
FIG. 8 is a graphic representation of proliferation of bone marrow granulocyte-macrophage colony forming cells by G-CSF and underivatized, aqueous soluble β(1,3)-glucan in mice. Saline=saline; β(1,3)-glucan=2 mg/kg underivatized, aqueous soluble β(1,3)-glucan on day 0; and G-CSF=125 ug/kg/day on days −3, −2, and −1.

EXAMPLE 6 Effects of Recombinant Human G-CSF and Underivatized. Aqueous Soluble β(1,3)-glucan Mobilization Protocols on the Proliferation of Bone Marrow Granulocyte-Macrophage Colony-Forming Cells in Mice Groups of three C3H/HeN female mice were injected for three consecutive days (days −3, −2, −1) with G-CSF (125 ug/kg/d, subcutaneously); injected on day 0 with underivatized, aqueous soluble β(1,3)-glucan (2 mg/kg, intravenously); or injected with saline. On day 0, bone marrow was collected 30 minutes after underivatized, aqueous soluble β(1,3)-glucan treatment and cultured for granulocyte-macrophage colony-forming cells (GM-CFC) in the presence of recombinant murine granulocyte-macrophage colony-stimulating factor (GM-CSF). Data represent the mean +/− standard deviation of triplicate cultures and shown in FIG. 8. Although increases in bone marrow GM-CFC numbers typically accompany G-CSF-induced progenitor cell mobilization protocols, increased bone marrow progenitor cell numbers were not seen with the underivatized, aqueous soluble β(1,3)-glucan-induced mobilization protocol, suggesting that underivatized, aqueous soluble β(1,3)-glucan mobilizes progenitor cells by a different mechanism than that of CSFs; this likely facilitates the ability of these agents to work in combination to enhance progenitor cell mobilization beyond that observed with either agent alone.

Figure 9:
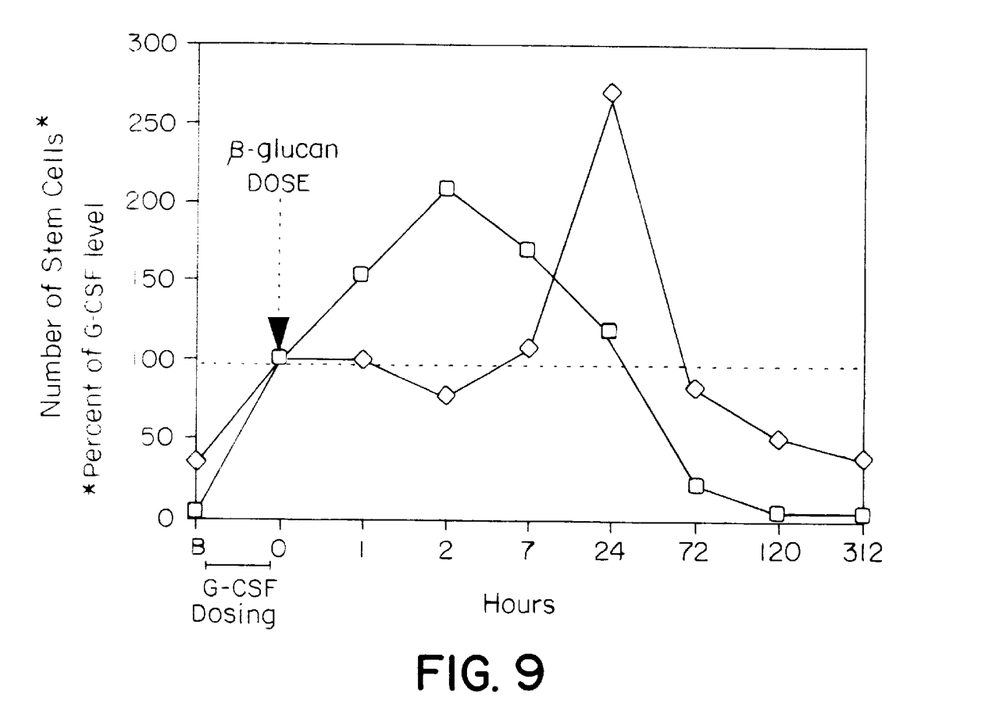
FIG. 9 is a graphic representation of the effect of underivatized, aqueous soluble β(1,3)-glucan and G-CSF on peripheral blood GM-CFC mobilization and CD34+ progenitor cells over time in a human subject receiving 1.5 mg/kg underivatized, aqueous soluble β(1,3)-glucan. Circles=CD34+ progenitor cells, squares=GM-CFC.

EXAMPLE 7 Mobilization of Peripheral Blood Progenitor Cells by the Combination of Recombinant G-CSF and Underivatized, Aqueous Soluble β(1,3)-glucan in Normal Human Volunteers A randomized, double-blind, placebo-controlled clinical trial was conduced in healthy males to evaluate the ability of underivatized, aqueous soluble β(1,3)-glucan to mobilize PBPC in the presence of G-CSF. All subjects received G-CSF (5 µg/kg/day) for 5 days. On day 5 coincidental with the expected peak of G-CSF-induced mobilization, either saline or underivatized, aqueous soluble β(1,3)-glucan was administered as a single infusion of 0.75, 1.5 or 2.5 mg/kg. Venous blood was collected at various times following administration of saline or underivatized, aqueous soluble β(1,3)-glucan. The PBPC mobilization potential of G-CSF and underivatized, aqueous soluble β(1,3)-glucan was evaluated based on peripheral GM-CFC levels and peripheral blood CD34+ mononuclear cells. The time course of the mobilization for a subject receiving 1.5 mg/kg of underivatized, aqueous soluble β(1,3)-glucan is shown in FIG. 9. Within two hours after underivatized, aqueous soluble β(1,3)-glucan treatment approximately 100% more CD34+ cells were mobilized by the combined treatment than by G-CSF alone and by 24 hours after underivatized, aqueous soluble β(1,3)-glucan treatment approximately 20% more GM-CFC were mobilized by the combined treatment than by G-CSF alone.

EXAMPLE 8 Protocol for Autologous Transplant of Hematopoietic Progenitor Cells, by Mobilization of Cells with β(1,3)-glucan and Expansion of Cells in vitro with Growth Factor and β(1,3)-glucan For patients preparing to undergo cytoreductive therapy who require an autologous transplant of hematopoietic progenitor cells, the following treatment protocol is used. Patients are administered underivatized, aqueous soluble β(1,3)-glucan at a dose of 0.75 to 2.25 mg/kg as a single intravenous infusion. After pre-treatment, peripheral blood is collected and hematopoietic progenitor cells are isolated by a leukophoresis technique, such as that described in Kessinger et al., *Blood* 74:1260, (1989).

The progenitor cells are cultured and expanded for 7–10 days in the presence of a growth factor such as GM-CSF in the presence or absence of underivatized, aqueous soluble β(1,3)-glucan. Shortly before the end of the culturing period, the patient undergoes the cytoreductive chemotherapy treatment. After the cell expansion is complete, the hematopoietic progenitor cells are washed and prepared for administration to the patient and are reinfused into the patient to effect hematopoietic reconstitution.

EXAMPLE 9 Protocol for Autologous Transplant of Hematopoietic Progenitor Cells, by Mobilization of Cells with Growth Factor and β(1.3)-glucan, and Expansion of Cells in vitro with Growth Factor and β(1,3)-glucan For patients preparing to undergo cytoreductive therapy who require an autologous transplant of hematopoietic progenitor cells, the following treatment protocol is used. Patients are administered a growth factor such as G-CSF for 5 days at a dose of 5 µg/kg/day subcutaneously and on day 5 receive an infusion of underivatized, aqueous soluble β(1,3)-glucan intravenously. Following pre-treatment, peripheral blood is collected and hematopoietic progenitor cells are isolated and cultured as described in Example 8. Within a few days after the patient receives the cytoreductive therapy, the expanded hematopoietic progenitor cells are reinfused into the patient to effect hematopoietic reconstitution.

EXAMPLE 10 Protocol for Autologous Transplant of Bone Marrow Cells

For patients preparing to undergo cytoreductive therapy, a treatment protocol using bone marrow cells can be followed. The treatment protocol is as described in Example 8 or 9, except that, following pre-treatment, bone marrow cells are removed instead of peripheral blood precursor cells. The bone marrow cells are isolated and cultured as described in Example 8 or 9. Within a few days after the patient receives the cytoreductive therapy, the expanded bone marrow cells are reinfused into the patient to effect hematopoietic reconstitution.

EXAMPLE 11 Alternate Protocol for Autologous Transplant of Bone Marrow Cells

For patients preparing to undergo cytoreductive therapy, the following, alternate treatment protocol using bone marrow cells can be followed. The treatment protocol is as described in Examples 8 or 9, except underivatized, aqueous soluble β(1,3)-glucan is administered at the time of autologous transplant to facilitate the reconstitution of hematopoietic progenitor cells. Alternatively, growth factors are administered concurrently with the underivatized, aqueous soluble β(1,3)-glucan until myeloid recovery is achieved.

Equivalents

Those skilled in the art will recognize, or be able to ascertain using no more than routine experimentation, many equivalents to the specific embodiments described herein. Such equivalents are intended to be encompassed by the following claims.

What is claimed is:

1. A method for facilitating hematopoietic reconstitution of peripheral blood precursor cells in a mammal's hematopoietic organs, comprising:
   a) administering to the mammal an effective amount of an underivatized, aqueous soluble β(1,3)-glucan in a triple helix conformation that is sufficient to cause the peripheral blood precursor cells to mobilize from hematopoietic organs into the mammal's peripheral circulation, thereby elevating the level of circulating peripheral blood precursor cells, wherein the β(1,3)-glucan does not stimulate or prime the production of proinflammatory cytokines, in vitro or in vivo;
   b) isolating mobilized peripheral blood precursor cells from the peripheral circulation of the mammal; and
   c) infusing the isolated mobilized peripheral blood precursor cells into the mammal.

2. The method of claim 1, further comprising administering a growth factor prior to or concurrently with administering the β(1,3)-glucan.

3. The method of claim 2, wherein the growth factor is selected from the group consisting of G-CSF, GM-CSF, IL-3, GM-CSF/IL-3 fusion proteins, FLK-2/FLT-3 ligand, stem cell factor, IL-6, IL-11, TPO and combinations thereof.

4. The method of claim 1, wherein the peripheral blood precursor cells are progenitor cells.

5. The method of claim 1, wherein the peripheral blood precursor cells are stem cells.

6. A method for inducing mobilization of hematopoietic progenitor cells in a mammal, comprising:
   a) administering to the mammal an effective amount of an underivatized aqueous soluble β(1,3)-glucan in a triple helix conformation that is sufficient to induce mobilization of hematopoietic progenitor cells from hematopoietic organs into the mammal's peripheral circulation;
   b) isolating mobilized hematopoietic progenitor cells from the mammal; and
   c) infusing the isolated mobilized hematopoietic progenitor cells into a mammal;
   wherein the β(1,3)-glucan does not stimulate or prime the production of proinflammatory cytokines, in vitro or in vivo.

7. The method of claim 6, wherein the hematopoietic progenitor cells are obtained from peripheral blood.

8. The method of claim 6, wherein the hematopoietic progenitor cells are obtained from bone marrow.

9. The method of claim 6, further comprising subsequently treating the mammal with a growth factor after infusing the isolated mobilized hematopoietic progenitor cells.

10. The method of claim 9, further comprising administering a growth factor prior to or concurrently with administering the β(1,3)-glucan that is administered, subsequent to infusing the isolated mobilized hematopoietic progenitor cells.

11. The method of claim 10, wherein the growth factor is selected from the group consisting of G-CSF, GM-CSF, IL-3, GM-CSF/IL-3 fusion proteins, FLK-2/FLT-3 ligand,, stem cell factor, IL-6, IL-11, TPO and combinations thereof.

12. The method of claim 6, further comprising expanding the isolated mobilized hematopoietic progenitor cells before infusing the cells.

13. A method for obtaining a therapeutically effective level of peripheral blood precursor cells, comprising:
  a) administering to the mammal an effective amount of an underivatized, aqueous soluble β(1,3)-glucan in a triple helix conformation that is sufficient to cause the peripheral blood precursor cells to mobilize from hematopoietic organs into mammal's peripheral circulation, wherein the β(1,3)-glucan does not stimulate or prime the production of proinflammatory cytokines, in vitro or in vivo; and
  b) isolating mobilized peripheral blood precursor cells from the peripheral circulation of the mammal to obtain a therapeutically effective level of said cells.

14. The method of claim 13, wherein the effective amount of the underivatized, aqueous soluble β(1,3)-glucan is administered in a single dose or a series of doses.

15. A method for obtaining a therapeutically effective level of ex vivo expanded cells from a population of peripheral blood precursor cells, comprising:
  a) administering to the mammal an effective amount of an underivatized, aqueous soluble β(1,3)-glucan in a triple helix conformation that is sufficient to cause the peripheral blood precursor cells to mobilize from the hematopoietic organs into the mammal's peripheral circulation, wherein the β(1,3)-glucan does not stimulate or prime the production of proinflammatory cytokines, in vitro or in vivo;
  b) isolating mobilized peripheral blood precursor cells from the peripheral circulation of the mammal; and
  c) causing the isolated mobilized peripheral blood precursor cell population to expand to thereby obtain a therapeutically effective level of said cells.

16. The method of claim 15, wherein the effective amount of the underivatized, aqueous soluble β(1,3)-glucan is administered in a single dose or a series of doses.

17. A method for obtaining a therapeutically effective level of peripheral blood precursor cells, comprising:
  a) administering to the mammal an effective amount of a growth factor which induces mobilization of peripheral blood precursor cells and an underivatized, aqueous soluble β(1,3)-glucan in a triple helix conformation that is sufficient to cause the peripheral blood precursor cells to mobilize from hematopoietic organs into the mammal's peripheral circulation, wherein the β(1,3)-glucan does not stimulate or prime the production of proinflammatory cytokines, in vitro or in vivo; and
  b) isolating mobilized peripheral blood precursor cells from the peripheral circulation of the mammal to obtain a therapeutically effective level of said cells.

18. The method of claim 17, wherein the growth factor is administered prior to or concurrently with administering the β(1,3)-glucan.

19. The method of claim 18, wherein the growth factor is selected from the group consisting of G-CSF, GM-CSF, IL-3, GM-CSF/IL-3 fusion proteins, FLK-2/FLT-3 ligand, stem cell factor, IL-6, IL 11, TPO and combinations thereof.

20. A method for obtaining a therapeutically effective level of ex vivo expanded cells from a population of peripheral blood precursor cells, comprising:
  a) administering to the mammal an effective amount of a growth factor which induces immobilization of peripheral blood precursor cells and an underivatized, aqueous soluble β(1,3)-glucan in a triple helix conformation that is sufficient to cause the peripheral blood precursor cells to mobilize from hematopoietic organs into the mammal's peripheral circulation, wherein the β(1,3)-glucan does not stimulate or prime the production of proinflammatory cytokines, in vitro or in vivo;
  b) isolating mobilized peripheral blood precursor cells from the peripheral circulation of the mammal; and
  c) causing the isolated mobilized peripheral blood precursor cell population to expand to thereby obtain a therapeutically effective level of said cells.

21. The method of claim 20, wherein the growth factor is administered prior to or concurrently with administering the β(1,3)-glucan.

22. The method of claim 21, wherein the growth factor is selected from the group consisting of G-CSP, GM-CSP, IL-3, GM-CSF/IL-3 fusion proteins, FLK-2/FLT-3 ligand, stein cell factor, IL-6, IL-11, TPO and combinations thereof.

* * * * *

UNITED STATES PATENT AND TRADEMARK OFFICE
CERTIFICATE OF CORRECTION

PATENT NO. : 6,117,850
DATED : September 12, 2000
INVENTOR(S) : Myra L. Patchen and Paul Bleicher It is certified that error appears in the above-identified patent and that said Letters Patent is hereby corrected as shown below:

Claim 11, Col. 11, line 14, delete the extra comma;

Claim 20, Col. 12, line 30, delete "immobilization" and insert ---mobilization---; and Claim 22, Col. 12, line 47, delete "GM-CSP" and insert ---GM-CSF---.

Signed and Sealed this

Twenty-fourth Day of April, 2001

Attest:

NICHOLAS P. GODICI

*Attesting Officer*       *Acting Director of the United States Patent and Trademark Office*